United States Patent
Pujol, Jr.

(10) Patent No.: US 10,143,821 B2
(45) Date of Patent: Dec. 4, 2018

(54) AUTOMATIC CONTROL OF TEMPERATURE IN A PATIENT CIRCUIT

(75) Inventor: John Raymond Pujol, Jr., Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 964 days.

(21) Appl. No.: 13/701,563

(22) PCT Filed: Apr. 27, 2011

(86) PCT No.: PCT/IB2011/051836
§ 371 (c)(1),
(2), (4) Date: Dec. 3, 2012

(87) PCT Pub. No.: WO2011/151739
PCT Pub. Date: Dec. 8, 2011

(65) Prior Publication Data
US 2013/0073013 A1    Mar. 21, 2013

Related U.S. Application Data

(60) Provisional application No. 61/351,326, filed on Jun. 4, 2010.

(51) Int. Cl.
*A61M 16/10* (2006.01)
*A61M 16/16* (2006.01)
*A61M 16/00* (2006.01)

(52) U.S. Cl.
CPC .... *A61M 16/1075* (2013.01); *A61M 16/0069* (2014.02); *A61M 16/024* (2017.08);
(Continued)

(58) Field of Classification Search
CPC ...... A61M 2016/0039; A61M 16/0066; A61M 16/1075; A61M 16/109; A61M 16/1095;
(Continued)

(56) References Cited

U.S. PATENT DOCUMENTS 4,621,632 A * 11/1986 Bartels .............. A61M 16/1075
128/203.17
5,673,687 A   10/1997 Dobson
(Continued)

FOREIGN PATENT DOCUMENTS

AU    2014204454 A1   7/2014
CN       101537221 A   9/2009
(Continued)

*Primary Examiner* — Gregory Anderson
*Assistant Examiner* — Elliot S Ruddie
(74) *Attorney, Agent, or Firm* — Michael W. Haas

(57) ABSTRACT

A method of automatically controlling the temperature of a patient circuit (56, 58) of a pressure support system (50) includes determining (directly measuring or estimating/deriving) one or more environmental parameters relating to environmental conditions around the pressure support system, such as ambient temperature and/or ambient humidity, determining a desired temperature based on at least the one or more environmental parameters, and controlling the operation of a heating apparatus (70) operatively associated with the patient circuit based on the desired temperature. Also, a pressure support system implementing the method.

18 Claims, 3 Drawing Sheets

(52) U.S. Cl.
CPC ...... *A61M 16/1095* (2014.02); *A61M 16/161* (2014.02); *A61M 16/0066* (2013.01); *A61M 2016/0039* (2013.01); *A61M 2205/3372* (2013.01)

(58) Field of Classification Search
CPC ................ A61M 16/16; A61M 16/161; A61M 2205/3368; A61M 2205/3372; A61M 2205/3653; A61M 2205/502
USPC .................................................... 128/230.27
See application file for complete search history.

(56) References Cited

U.S. PATENT DOCUMENTS

| | | | | |
|---|---|---|---|---|
| 8,225,796 | B2* | 7/2012 | Davenport et al. ...... | 128/207.18 |
| 9,168,350 | B2* | 10/2015 | Payton .............. | A61M 16/0666 |
| 2004/0221844 | A1* | 11/2004 | Hunt et al. ............... | 128/204.17 |
| 2007/0215147 | A1 | 9/2007 | Ho | |
| 2007/0221224 | A1 | 9/2007 | Pittman | |
| 2008/0051674 | A1* | 2/2008 | Davenport ............. | A61B 5/087 |
| | | | | 600/561 |
| 2008/0190427 | A1* | 8/2008 | Payton .............. | A61M 16/0666 |
| | | | | 128/203.27 |
| 2008/0308100 | A1 | 12/2008 | Pujol | |
| 2009/0071479 | A1 | 3/2009 | Nguyen | |
| 2009/0223514 | A1 | 9/2009 | Smith | |
| 2010/0132707 | A1 | 6/2010 | Muller | |
| 2011/0120462 | A1* | 5/2011 | Tatkov ............... | A61M 16/1075 |
| | | | | 128/203.14 |
| 2011/0253136 | A1* | 10/2011 | Sweeney ............... | A61M 16/16 |
| | | | | 128/203.12 |

FOREIGN PATENT DOCUMENTS

| | | |
|---|---|---|
| DE | 102006019402 | 10/2007 |
| EP | 0535952 B1 | 12/1997 |
| EP | 1197237 B1 | 3/2007 |
| JP | 2003507138 A | 2/2003 |
| WO | WO2009094532 A1 | 7/2009 |
| WO | WO2010016838 A1 | 2/2010 |

* cited by examiner

AUTOMATIC CONTROL OF TEMPERATURE IN A PATIENT CIRCUIT

CROSS-REFERENCE TO RELATED APPLICATIONS

This patent application claims the priority benefit under 35 U.S.C. § 371 of international patent application no. PCT/IB2011/051836, filed Apr. 27, 2011, which claims the priority benefit under 35 U.S.C. § 119(e) of U.S. Provisional Application No. 61/351,326 filed on Jun. 4, 2010, the contents of which are herein incorporated by reference.

BACKGROUND OF THE INVENTION

1. Field of the Disclosure

The present invention relates to airway pressure support systems, and, more particularly, to an airway pressure support system in which the temperature of the patient breathing circuit is automatically controlled based on environmental conditions and, optionally, other conditions such as gas steam conditions.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

It is well known to treat sleep disordered breathing by applying a positive air pressure (PAP) to the patient's airway. This positive pressure effectively "splints" the airway, thereby maintaining an open passage to the lungs. In one type of PAP therapy, known as continuous positive air pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Humidifiers are frequently provided between or integral with a PAP machine and the user interface in order to humidify the otherwise relatively-dry compressed air generated by the PAP machine. Within the humidifier, water is allowed to evaporate to produce vapor within a reservoir while breathing gas is passed over the surface of the water. Increased water vapor within the reservoir increases the capability to provide more humidity to the gas that is delivered to a user. In a heated passover type of humidifier, this increase in gas stream humidity is accompanied by an increase in the gas stream temperature. When the ambient temperature around the PAP machine is below the gas stream temperature, condensation can form on the inside of the patient breathing circuit.

It is presently known to heat the patient breathing circuit in order to reduce the formation of condensation on and/or within the patient breathing circuit. In current systems, the patient circuit is heated by providing a constant amount of heat to the patient circuit in an effort to maintain a constant temperature. Current systems do not, however, automatically control the heating of the patient breathing circuit based on factors including the environmental conditions around the PAP machine.

SUMMARY OF THE INVENTION

In one embodiment, a method of automatically controlling the temperature of a patient circuit of a pressure support system is provided that includes determining (directly measuring or estimating/deriving) one or more environmental parameters relating to environmental conditions around the pressure support system, such as ambient temperature and/or ambient humidity, determining a desired temperature based on at least the one or more environmental parameters, and controlling the operation of a heating apparatus operatively associated with the patient circuit based on the desired temperature.

In another embodiment, a pressure support system is provided that includes a pressure generating system, a patient circuit operatively coupled to the pressure generating system, a humidifier structured to humidify a pressurized gas stream generated by the pressure generating system, a heating apparatus operatively associated with the patient circuit, and a controller operatively coupled to the pressure generating system and the heating apparatus. The controller is adapted to control the temperature of the patient circuit using the method just described.

In still another embodiment, a patient circuit heating system for a pressure support system having a patient circuit is provided that includes a heating apparatus structured to be operatively associated with the patient circuit, and a controller operatively coupled to the heating apparatus. The controller is adapted to control a temperature of the patient circuit by determining one or more environmental parameters relating to environmental conditions around the pressure support system, determining a desired temperature based on at least the one or more environmental parameters, and controlling operation of the heating apparatus based on the desired temperature.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
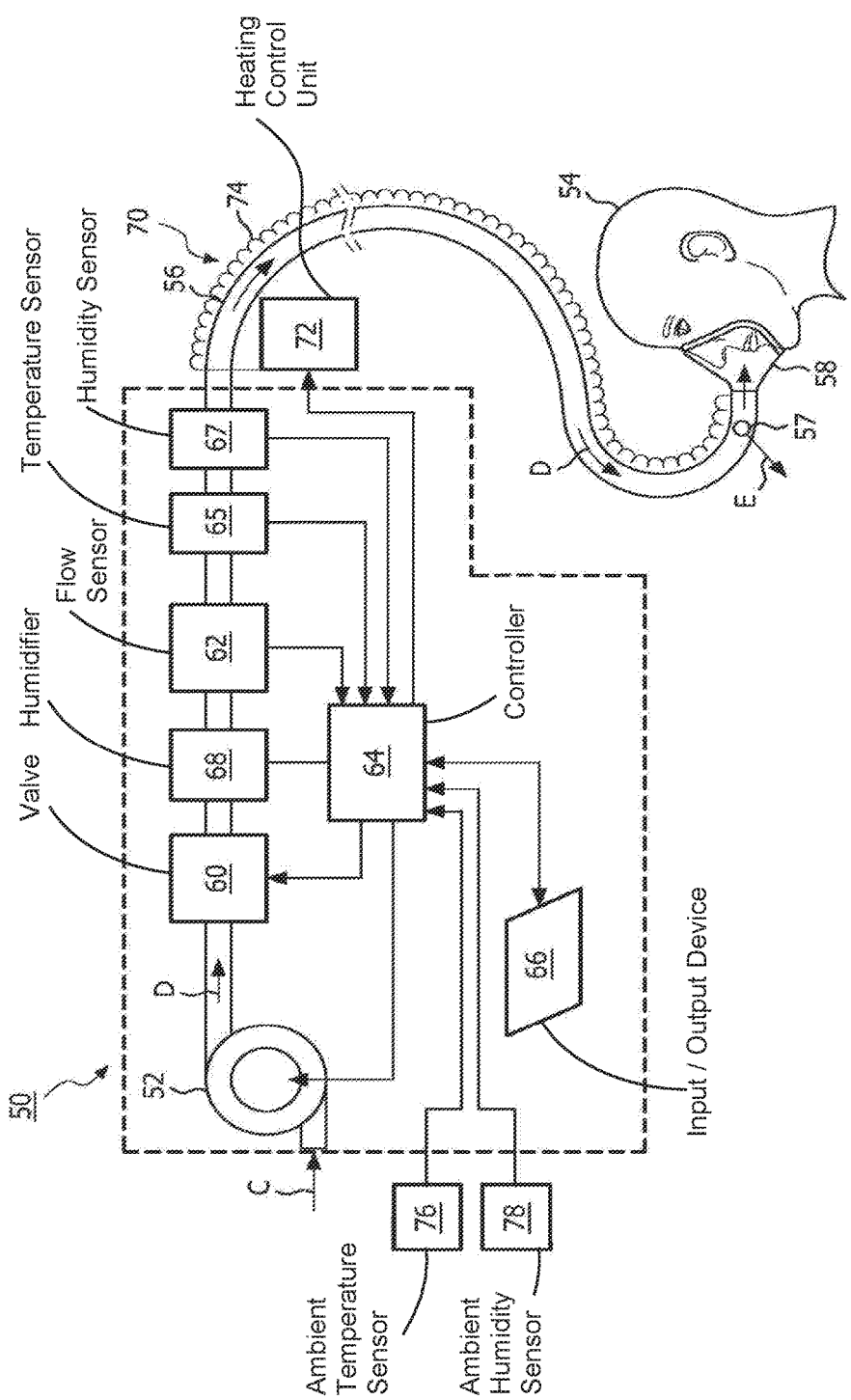
FIG. 1 is a schematic diagram of a pressure support system according to one particular, non-limiting embodiment in which the present invention in its various embodiments may be implemented.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of pressure support system 50 according to one particular, non-limiting embodiment in which the present invention in its various embodiments may be implemented. Referring to FIG. 1, pressure support system 50 includes gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of patient 54 at relatively higher and lower pressures, i.e., generally equal to or above ambient atmospheric pressure. In the exemplary embodiment, gas flow generator 52 is capable of providing a flow of breathing gas ranging in pressure from 3-30 cmH$_2$O. The pressurized flow of breathing gas, generally indicated by arrow D from gas flow generator 52, is delivered via delivery conduit 56 to breathing mask or patient interface 58 of any known construction, which is typically worn by or otherwise attached to patient 54 to communicate the flow of breathing gas to the airway of patient 54. Delivery conduit 56 and patient interface device 58 are typically collectively referred to as a patient circuit.

Pressure support system 50 shown in FIG. 1 is what is known as a single-limb system, meaning that the patient circuit includes only delivery conduit 56 connecting patient 54 to pressure support system 50. As such, exhaust vent 57 is provided in delivery conduit 56 for venting exhaled gasses from the system as indicated by arrow E. It should be noted that exhaust vent 57 can be provided at other locations in addition to or instead of in delivery conduit 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery conduit and an exhaust conduit connected to patient 54. In a two-limb system (also referred to as a dual-limb system), the exhaust conduit carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal/oral mask. It is to be understood, however, that patient interface 58 can include a nasal mask, nasal pillows, a tracheal tube, an endotracheal tube, or any other device that provides a suitable gas flow communicating function. Also, for purposes of the present invention, the phrase "patient interface" can include delivery conduit 56 and any other structures that connect the source of pressurized breathing gas to patient 54.

In the illustrated embodiment, pressure support system 50 includes a pressure controller in the form of valve 60 provided in delivery conduit 56. Valve 60 controls the pressure of the flow of breathing gas from flow generator 52 that is delivered to patient 54. For present purposes, flow generator 52 and valve 60 are collectively referred to as a pressure generating system because they act in concert to control the pressure and/or flow of gas delivered to patient 54. However, it should be apparent that other techniques for controlling the pressure of the gas delivered to patient 54, such as varying the blower speed of flow generator 52, either alone or in combination with a pressure control valve, are contemplated by the present invention. Thus, valve 60 is optional depending on the technique used to control the pressure of the flow of breathing gas delivered to patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes flow sensor 62 that measures the flow of the breathing gas within delivery conduit 56. In the particular embodiment shown in FIG. 1, flow sensor 62 is interposed in line with delivery conduit 56, most preferably downstream of valve 60. Flow sensor 62 generates a flow signal, $Q_{measured}$, that is provided to controller 64 and is used by controller 64 to determine the flow of gas at patient 54 ($Q_{patient}$).

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 1, and unknown leaks from the system, such a leaks at the mask/patient interface. The present invention contemplates using any known or hereafter developed technique for calculating leak flow $Q_{leak}$, and using this determination in calculating $Q_{patient}$ based on $Q_{measured}$. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 54 are contemplated by the present invention, such as, without limitation, measuring the flow directly at patient 54 or at other locations along delivery conduit 56, measuring patient flow based on the operation of flow generator 52, and measuring patient flow using a flow sensor upstream of valve 60.

Pressure support system 50 also includes temperature sensor 65 operatively coupled to delivery conduit 56 for detecting the temperature of the gas stream output by pressure support system 50, and humidity sensor 67 operatively coupled to delivery conduit 56 for detecting the humidity of the gas stream output by pressure support system 50. Temperature sensor 65 and humidity sensor 67 are each operatively coupled to controller 64. In the embodiment shown, temperature sensor 65 and humidity sensor 67 are provided within the main housing of pressure support system 50. Alternatively, either or both of temperature sensor 65 and humidity sensor 67 may be provided in or coupled to the patient circuit.

Controller 64 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 50, including automatically controlling the temperature of the patient circuit based at least on certain environmental conditions as described in greater detail herein.

Input/output device 66 is provided for setting various parameters used by pressure support system 50, as well as for displaying and outputting information and data to a user, such as a clinician or caregiver.

In the illustrated embodiment, pressure support system 50 also includes humidifier 68 provided in the main housing of pressure support system 50. Alternatively, humidifier 68 may be separate from and located external to the main housing. Humidifier 68 further improves comfort by providing moisture in the supplied gas. In the exemplary embodiment, humidifier 68 is a passover type humidifier. U.S. Patent Application Publication No. 2007/0169776, incorporated herein by reference in its entirety, discloses an exemplary humidifier device suitable for use in the present invention. Humidifier devices having alternative designs may also be used.

Pressure support system 50 further includes patient circuit heating apparatus 70, which in the illustrated embodiment comprises heating control unit 72 operatively coupled to heating coil 74. Heating coil 74 is positioned adjacent to or within delivery conduit 56 of the patient circuit and is structured to heat the patient circuit under the control of heating control unit 72. Heating control unit 72 is operatively coupled to and controlled by controller 64. The patient circuit heating apparatus 70 including heating control unit 72 and heating coil 74 is but one example of a suitable heating apparatus, and it will be understood that other heating apparatuses may be employed ion the present invention.

In the illustrated, non-limiting embodiment of the present invention, pressure support system 50 essentially functions as a CPAP pressure support system, and, therefore, includes all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Finally, pressure support system 50 also includes ambient temperature sensor 76 and ambient humidity sensor 78. Both ambient temperature sensor 76 and ambient humidity sensor 78 are operatively coupled to controller 64. Ambient temperature sensor 76 measures the ambient temperature around pressure support system 50, and thus the temperature of the gas entering pressure support system 50, and provides that information to controller 64. Ambient humidity sensor 78 measures the ambient humidity around pressure support system 50, and thus the humidity of the gas entering pressure support system 50, and provides that information to controller 64. In the illustrated embodiment, ambient temperature sensor 76 and ambient humidity sensor 78 are located adjacent to the inlet of gas flow generator 52.

As noted elsewhere herein, according to the methodology of the present invention (implemented in software executable by controller 64 for controlling pressure support system 50), pressure support system 50 controls the heating of the patient circuit (by controlling operation of patient circuit heating apparatus 70 including heating control unit 72 and heating coil 74) based on certain measured or estimated environmental conditions relating to pressure support system 50. More specifically, based on at least the environmental inputs just described, controller 64 determines a desired temperature for the patient circuit and then outputs appropriate control signals/parameters (e.g., a current level, duty cycle, PWM controls, etc.) to heating control unit 72 to cause heating coil 74 to attempt to heat the patient circuit to that desired temperature. In the exemplary embodiment, the desired temperature is the minimum temperature that the patient circuit needs to achieve to prevent rainout in the patient circuit (i.e., to have a condensation free patient circuit).

In another embodiment, the desired temperature is a temperature that limits condensation in the patient circuit to an acceptable degree, such as, without limitation, 95% relative humidity. Also in the exemplary embodiment, the environmental conditions include ambient temperature and/or ambient humidity, although other environmental conditions (sensed by appropriate sensors or estimated from other data) may also be used, such as barometric pressure. As described in greater detail below, ambient temperature may be directly measured by ambient temperature sensor 76 (as in the illustrated embodiment of FIG. 1), or, alternatively, may be estimated or derived based on other data obtained by pressure support system 50. Similarly, ambient humidity may be directly measured by ambient humidity sensor 78 (as in the illustrated embodiment of FIG. 1), or, alternatively, may be estimated or derived based on other data obtained by pressure support system 50.

In addition, in one particular embodiment, pressure support system 50 also controls the heating of the patient circuit as described above (i.e., determining the desired temperature and then causing the patient circuit heating apparatus 70 to attempt to heat the patient circuit to that temperature) based on either or both of certain measured or estimated gas stream conditions, and certain physical and/or operational characteristics of the patient circuit. The gas stream conditions may include, without limitation, the temperature and/or humidity of the gas stream output by pressure support system 50. Such gas stream temperature may be directly measured by temperature sensor 65 (as in the illustrated embodiment of FIG. 1), or, alternatively, may be estimated or derived based on other data obtained by pressure support system 50. Similarly, the humidity of the gas stream output by pressure support system 50 may be directly measured by humidity sensor 67 (as in the illustrated embodiment of FIG. 1), or, alternatively, may be estimated or derived based on other data obtained by pressure support system 50. The physical and/or operational characteristics of the patient circuit may include, without limitation, one or more of the thermal conductivity of the patient circuit tubing, the length and surface area of the patient circuit tubing and the actual or estimated gas stream flow rate through the patient circuit tubing. In the exemplary embodiment, the physical and/or operational characteristics of the patient circuit are determined and loaded into controller 64 in advance.

Figure 2:
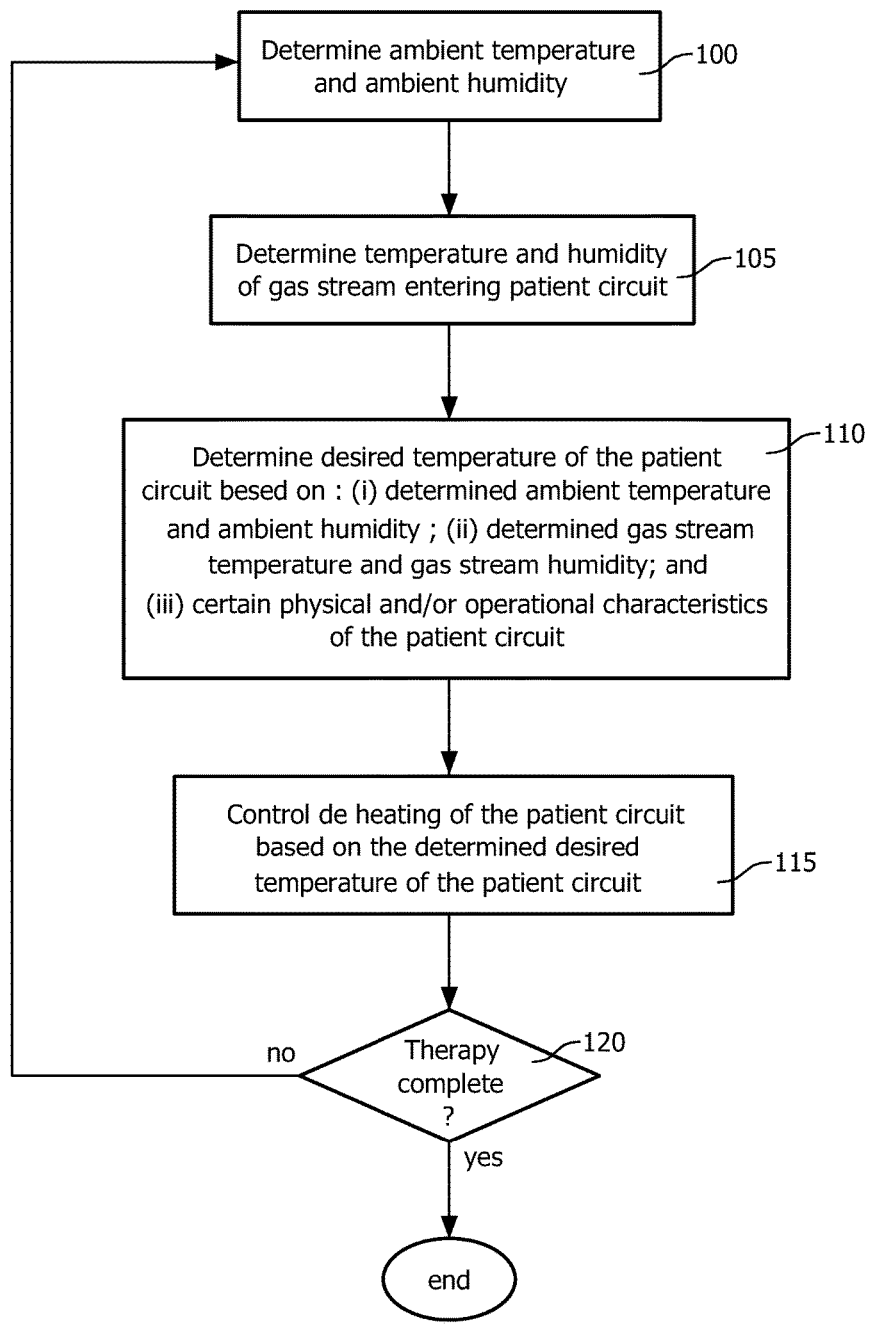
FIG. 2 is a flowchart showing a method of automatically controlling the temperature of a patient circuit according to one particular, non-limiting embodiment of the invention.

FIG. 2 is a flowchart showing a method of automatically controlling the temperature of a patient circuit according to one particular, non-limiting embodiment of the invention. The method shown in FIG. 2 may be implemented in the exemplary pressure support system 50 shown in FIG. 1 (or in another suitable pressure support system) through appropriate programming of controller 64. For illustrative purposes, the method will be described herein as implemented in the pressure support system 50.

The method begins at step 100, wherein the ambient temperature and the ambient humidity around pressure support system 50 are determined. In the exemplary embodiment, the ambient temperature is measured by ambient temperature sensor 76 and the ambient humidity is measured by ambient humidity sensor 78. Alternatively, ambient temperature sensor 76 and ambient humidity sensor 78 may be omitted, and the ambient temperature and the ambient humidity may be estimated or derived from the operating parameters of pressure support system 50 (e.g., pressure level) and/or from data that is measured/sensed by pressure support system 50 (such as, without limitation, temperature and humidity as measured by temperature sensor 65 and humidity sensor 67) using any of a number of known methods of back estimation/derivation.

Next, at step 105, the temperature and humidity of the gas output by pressure support system 50 and entering delivery conduit 56 is determined. In the exemplary embodiment, this gas stream temperature is measured by temperature sensor 65 and this gas stream humidity is measured by humidity sensor 67. Alternatively, temperature sensor 65 and humidity sensor 67 may be omitted, and the gas stream temperature and the gas stream humidity may be estimated or derived from the operating parameters of pressure support system 50 and the ambient temperature measured by ambient temperature sensor 76 and/or ambient humidity as measured by ambient humidity sensor 78 using any of a number of known methods of feed forward estimation/derivation. One such suitable method is described in United States Patent Application Publication No. 2008/0308100, the disclosure of which is incorporated herein by reference.

Next, at step 110 in the illustrated embodiment, a desired temperature for the patient circuit including delivery conduit 56 is determined based on (i) the determined ambient temperature and ambient humidity, (ii) the determined gas stream temperature and gas stream humidity, and (iii) one or more physical and/or operational characteristics of the patient circuit. With respect to (iii), the physical characteristics of the patient circuit may include one or more of the thermal conductivity, length or surface area of the patient circuit tubing, and the operational characteristics of the patient circuit may include the actual or estimated flow rate of the breathing gas through the patient circuit tubing. As noted elsewhere herein, in the exemplary embodiment, the desired temperature is the minimum temperature that the patient circuit (particularly delivery conduit 56) needs to achieve to prevent rainout in the patient circuit (i.e., to have a condensation free patient circuit, particularly delivery conduit 56). Knowing the properties of air and water and using the data of (i), (ii) and (iii) above, that minimum temperature may be determined/calculated in a number of different ways that are within the ordinary skill in the art (without undue experimentation). Thus, such methods will not be discussed in great detail herein. In one example methodology, that minimum temperature may be determined/calculated in the following manner. Knowing the ambient temperature and/or the ambient humidity along with the gas stream temperature and/or gas stream humidity, the temperature of the delivery conduit 56 can be maintained above the dew point or saturation temperature of the gas stream as determined using psychrometric data.

Following step 110, the method proceeds to step 115, wherein the heating of the patient circuit (particularly delivery conduit 56) is controlled by controller 64 based on the determined desired temperature. In the exemplary embodiment, controller 64 outputs appropriate control signals/parameters (e.g., current level, duty cycle, PWM controls, etc., depending on the specifics of the heating control unit 72) to heating control unit 72 to cause heating coil 74 to attempt to heat the patient circuit (particularly delivery conduit 56) to that desired temperature. Then, at step 120, a determination is made as to whether therapy is complete. If the answer is yes, then the method ends. If the answer is no, then the method returns to step 100 and repeats continuously throughout the therapy session.

Numerous variations of how to determine the desired temperature (step 110) are also possible. For example, only a single environmental condition (e.g., temperature or humidity only) may be employed in conjunction with one or both of gas stream conditions and physical and/or operational characteristics of the patient circuit. In addition, one or more environmental conditions may be employed alone (i.e., without the gas stream conditions and physical and/or operational characteristics of the patient circuit). Alternative environmental conditions, such as barometric pressure, may be measured or estimated and employed alone or with the other environmental conditions described herein. Still other variations are possible within the scope of the present invention and will be apparent to those of skill in the art.

Figure 3:
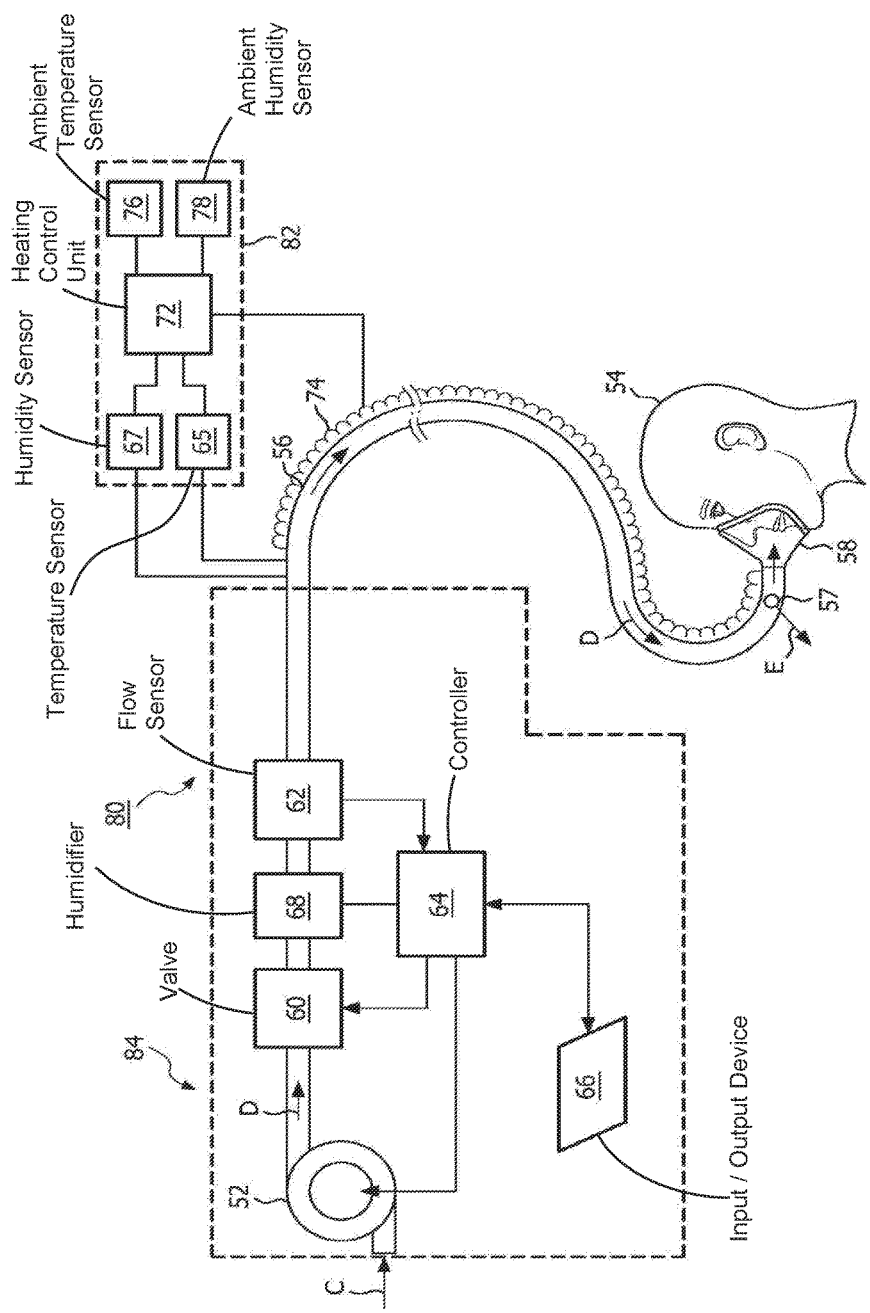
FIG. 3 is a schematic diagram of a pressure support system according to an alternative particular, non-limiting embodiment in which the present invention in its various embodiments may be implemented.

FIG. 3 is a schematic diagram of pressure support system 80 according to an alternative exemplary, non-limiting embodiment in which the present invention in its various embodiments may be implemented. Pressure support system 80 includes a number of the same components as pressure support system 50, and like components are labeled with like reference characters. However, as shown in FIG. 3, in pressure support system 80, heating control unit 72, temperature sensor 65, humidity sensor 67, ambient temperature sensor 76 and ambient humidity sensor 78 are not operatively coupled to controller 64. Instead, those components are provided as part of a self standing system 82 that could be selectively coupled to and used as an accessory to an exiting pressure support system 84. Heating control unit 72 is operatively coupled to and controls heating coil 74. Heating coil 74 may be selectively operatively coupled to delivery conduit 56. In addition, heating control unit 72 in this embodiment includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of system 82, including automatically controlling the temperature of the patient circuit based at least on certain environmental conditions as described in greater detail herein based on information received from temperature sensor 65, humidity sensor 67, ambient temperature sensor 76 and ambient humidity sensor 78.

Thus, the present invention provides a method of automatic patient circuit temperature control that consistently provides the appropriate amount of heating to the patient circuit to avoid/limit or completely eliminate condensation within the patient circuit regardless of changes in environmental conditions in the room in which the pressure support system is being used and optionally other conditions such as gas stream conditions. In doing so, the automatic patient circuit temperature control minimizes the convective heating of the gas being delivered to the patient by not maintaining a constant patient circuit temperature. Also, by optimally controlling the temperature being maintained by the heated patient circuit, the power consumption by the patient circuit can be minimized. Also, the automatic patient circuit temperature control maintains the proper circuit temperature as gas stream conditions change as a function of therapy changes from pressure support system 50.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory therapy system having a temperature controlled patient circuit, the system comprising: a pressure support system including: a pressure generator configured to generate a pressurized flow of breathable gas for delivery to an airway of a subject; the patient circuit configured to communicate the pressurized flow of breathable gas to the airway of the subject; and one or more sensors configured to generate output signals conveying information related to an ambient temperature around the pressure support system, an ambient humidity around the pressure support system, a temperature of the pressurized flow of breathable gas, and a humidity of the pressurized flow of breathable gas; and one or more processors configured by machine-readable instructions to: determine the ambient temperature and the ambient humidity around the pressure support system based on the output signals; determine the temperature and the humidity of the pressurized flow of breathable gas based on the output signals; determine a desired temperature for the patient circuit based on (i) the determined ambient temperature and ambient humidity, (ii) the determined temperature and humidity of the pressurized flow of breathable gas, and (iii) one or more physical characteristics of the patient circuit, the physical characteristics of the patient circuit including one or more of a thermal conductivity of the patient circuit, a length of the patient circuit, or a surface area of the patient circuit; and control an operation of a heating apparatus operatively associated with the patient circuit based on the determined desired temperature.

2. The system of claim 1, wherein the heating apparatus comprises a heating coil disposed adjacent to or with the patient circuit and wherein the one or more processors are configured such that controlling the operation of the apparatus comprises controlling one or more of a duty cycle, or one or more pulse width modulation parameters associated with the heating coil.

3. The system of claim 1, wherein desired temperature is a minimum temperature required to prevent condensation within the patient circuit.

4. The system of claim 1, wherein the pressure support system further comprises a flow sensor disposed in line with the patient circuit, the flow sensor configured to generate output signals conveying information related to a flow of the pressurized flow of breathable gas and wherein the one or more processors are further configured to:
determine, based on the flow sensor output signals, a flow rate of the pressurized flow of breathable gas; and
determine the desired temperature for the patient circuit based on the determined flow rate.

5. The system of claim 1, wherein the one or more sensors comprise one or more of a temperature sensor, a humidity sensor, an ambient temperature sensor, or an ambient humidity sensor removably coupled with the pressure support system.

6. A method for automatically controlling a temperature of a patient circuit with a patient circuit heating system, the patient circuit heating system comprising a pressure support system, one or more sensors, and one or more processors, the method comprising:
generating, with the one or more sensors, output signals conveying information related to an ambient temperature around the pressure support system, an ambient humidity around the pressure support system, a temperature of a pressurized flow of breathable gas generated by the pressure support system, and a humidity of the pressurized flow of breathable gas;

determining, with the one or more processors, the ambient temperature and the ambient humidity around the pressure support system based on the output signals;

determining, with the one or more processors, the temperature and the humidity of the pressurized flow of breathable gas based on the output signals;

determining, with the one or more processors, a desired temperature for the patient circuit based on (i) the determined ambient temperature and ambient humidity, (ii) the determined temperature and humidity of the pressurized flow of breathable gas, and (iii) one or more physical characteristics of the patient circuit, the physical characteristics of the patient circuit including one or more of a thermal conductivity of the patient circuit, a length of the patient circuit, or a surface area of the patient circuit; and controlling, with the one or more processors, an operation of a heating apparatus operatively associated with the patient circuit based on the determined desired temperature.

7. The method of claim 6, wherein the heating apparatus comprises a heating coil disposed adjacent to or with the patient circuit and wherein controlling the operation of the heating apparatus comprises controlling one or more of a duty cycle, or one or more pulse width modulation parameters associated with the heating coil.

8. The method of claim 6, wherein desired temperature is a minimum temperature required to prevent condensation within the patient circuit.

9. The method of claim 6, wherein the pressure support system further comprises a flow sensor disposed in line with the patient circuit, the flow sensor configured to generate output signals conveying information related to a flow of the pressurized flow of breathable gas, the method further comprising:

determining, with the one or more processors, a flow rate of the pressurized flow of breathable gas based on the flow sensor output signals; and determining, with the one or more processors, the desired temperature for the patient circuit based on the determined flow rate.

10. The method of claim 6, wherein the one or more sensors comprise one or more of a temperature sensor, a humidity sensor, an ambient temperature sensor, or an ambient humidity sensor removably coupled with the pressure support system.

11. A respiratory therapy system having a temperature controlled patient circuit, the system comprising:

a pressure support system including:

means for generating a pressurized flow of breathable gas for delivery to an airway of a subject; and means for communicating the pressurized flow of breathable gas to the airway of the subject;

means for determining an ambient temperature and an ambient humidity around the pressure support system;

means for determining a temperature and a humidity of the pressurized flow of breathable gas;

means for determining a desired temperature for the means for communicating based on (i) the determined ambient temperature and ambient humidity, (ii) the determined temperature and humidity of the pressurized flow of breathable gas, and (iii) one or more physical characteristics of the means for communicating, the physical characteristics of the means for communicating including one or more of a thermal conductivity of the means for communicating, a length of the means for communicating, or a surface area of the means for communicating; and means for controlling an operation of a heating apparatus operatively associated with the means for communicating based on the determined desired temperature.

12. The system of claim 11, wherein the heating apparatus comprises a heating coil disposed adjacent to or with the means for communicating and wherein the means for controlling the operation of a heating apparatus comprises means for controlling one or more of a duty cycle, or one or more pulse width modulation parameters associated with the heating coil.

13. The system of claim 11, wherein desired temperature is a minimum temperature required to prevent condensation within the means for communicating.

14. The system of claim 11, further comprising means for determining a flow rate of the pressurized flow of breathable gas; and means for determining the desired temperature for the means for communicating based on the determined flow rate.

15. The system of claim 11, further comprising one or more of a temperature sensor, a humidity sensor, an ambient temperature sensor, or an ambient humidity sensor removably coupled with the pressure support system.

16. The system of claim 1, wherein the physical characteristics of the patient circuit include one or more of the length of the patient circuit, or the surface area of the patient circuit.

17. The method of claim 6, wherein the physical characteristics of the patient circuit include one or more of the length of the patient circuit, or the surface area of the patient circuit.

18. The system of claim 11, wherein the physical characteristics of the patient circuit include one or more of the length of the patient circuit, or the surface area of the patient circuit.

* * * * *